United States Patent

Homoto et al.

[11] Patent Number: 5,849,160
[45] Date of Patent: Dec. 15, 1998

[54] PROCESS OF SEPARATING PENTAFLUOROETHANE AND PROCESS OF PRODUCING PENTAFLUOROETHANE USING THE SAME

[75] Inventors: Yukio Homoto; Takashi Shibanuma; Masanobu Nishitsuji, all of Osaka, Japan

[73] Assignee: Daikin Industries, Ltd., Osaka, Japan

[21] Appl. No.: 809,897

[22] PCT Filed: Oct. 6, 1995

[86] PCT No.: PCT/JP95/02048

§ 371 Date: Jul. 2, 1997

§ 102(e) Date: Jul. 2, 1997

[87] PCT Pub. No.: WO96/11176

PCT Pub. Date: Apr. 18, 1996

[30] Foreign Application Priority Data

Oct. 7, 1994 [JP] Japan .................................. 6-243907

[51] Int. Cl.⁶ ........................ B01D 3/00; C07C 17/383; C07C 19/08
[52] U.S. Cl. ................................. 203/87; 62/115; 95/39; 203/29; 203/39; 203/91; 570/177; 570/178
[58] Field of Search .............................. 203/2, 3, 91, 87, 203/29, 39; 570/168, 178, 177; 95/39; 62/115

[56] References Cited

U.S. PATENT DOCUMENTS 4,766,260  8/1988  Manzer et al. .
4,911,792  3/1990  Manzer et al. .
4,944,846  7/1990  Manzer et al. .
5,094,773  3/1992  Manzer et al. .
5,453,551  9/1995  Lacroix et al. ........................ 570/177
5,569,794  10/1996  Tang ...................................... 570/168

FOREIGN PATENT DOCUMENTS 503771  9/1992  European Pat. Off. .
0676386  10/1995  European Pat. Off. .
176434  7/1991  Japan .

Primary Examiner—Virginia Manoharan
Attorney, Agent, or Firm—Birch, Stewart, Kolasch & Birch, LLP

[57] ABSTRACT

Pentafluoroethane (HFC-125) is more effectively and more simply separated from a reaction mixture in a process of producing HFC-125.

A gas mixture containing perchloroethylene (PCE), HFC-125, hydrogen chloride (HCl) and hydrogen fluoride (HF) is passed through the first condensation stage to obtain the first vapor phase, which is passed through the second condensation stage to obtain the second vapor phase mainly containing HFC-125 and HCl and the second liquid phase, which is passed to a distillation stage to obtain a top fraction mainly containing HFC-125 and HCl and a bottom fraction containing the rest of the second liquid phase which bottom fraction is substantially free from HFC-125 and HCl, and HCl is separated out of the second vapor phase portion and the top fraction to obtain HFC-125, a concentration of PCE in the second liquid phase being such that it does not separate into immiscible liquid phases.

10 Claims, 6 Drawing Sheets

PROCESS OF SEPARATING PENTAFLUOROETHANE AND PROCESS OF PRODUCING PENTAFLUOROETHANE USING THE SAME

DESCRIPTION

1. Techincal Field

The present invention relates to a process of producing 1,1,1,2,2-pentafluoroethane (which is also referred to as "HFC-125" or "pentafluoroethane" herein and the attached claims). Particularly, the present invention relates to a process of effectively separating pentafluoroethane out of a reaction mixture comprising pentafluoroethane and a process of producing pentafluoroethane using such a separation process.

2. Background Art

Pentafluoroethane is prepared by reacting perchloroethylene (which is also referred to as "PCE" herein and the attached claims) and excessive hydrogen fluoride (which is also referred to as "HF" herein and the attached claims) (see U.S. Pat. No. 4,766,260). In that reaction, the following compounds are formed as by-products: 1,1-dichloro-2,2,2-trifluoroethane and 1,2-dichloro-1,1,2-trifluoroethane (which are also referred to as "dichlorotrifluoroethane" or "HFC-123" together as herein and the attached claims), 1,2,2,2-tetrafluoro-1-chloroethane and 1,1,2,2-tetrafluoro-1-chloroethane (which are also referred to as "tetrafluorochloroethane" or "HFC-124" together as herein and the attached claims) and hydrogen chloride (which is also referred to as "HCl" herein and the attached claims). Therefore, it is necessary to remove products except HFC-125.

As to separation of HFC-123 and HFC-124 out of HF, for example, a process has been known in which azeotropic distillation is used (see U.S. Pat. Nos. 5,094,773 and 4,944,846). An alternative process of separating produced HFC-123 and HFC-124 out of HF excessively present, a process has been known in which a mixture gas containing those components are condensed and divided into a liquid phase rich in HF and another liquid phase rich in HFC-123 and HFC-124, then the latter phase is subjected to distill off HFC-123 and HFC-124 as azeotrope mixtures with HF and remaining pure HFC-123 and HFC-124 are obtained (see U.S. Pat. No. 4,911,792). This process is characterized in that an organic phase as a lower layer (which corresponds to the phase rich in HFC-123 and HFC-124) contains HF of less than 15% by mole and an HF phase as an upper layer contains HF of not less than 93% by mole.

When the separation process as described above is applied to a reaction gas contains a large amount of HFC-125 as in the case of the production of HFC-125, a relatively large amount of HFC-125 is distributed in both of the upper and the lower layers. In order to recover HFC-125 from the gas mixture, the upper and lower layers separated into immiscible liquid phases should be subjected to distillation. Thus, a process including the liquid separation and the azeotropic distillation is not economical since facilities thereof are so complicated so that a capital cost is increased.

Thus, it has been desired to develop a process in which HFC-125 is separated and refined effectively, particularly in a simpler manner from a reaction mixture in the production of HFC-125.

DISCLOSURE OF INVENTION

The present inventors have found that a liquid mixture containing perchloroethylene, pentafluoroethane, hydrogen chloride and hydrogen fluoride has a composition range in which the mixture does not separate into immiscible liquid phases within an industrially operative temperature range, for example −30° to 90° C. (the composition range depends on a temperature a little, and is for example a composition range of which PCE concentration is not larger than about 3% by mole), and then reached the present invention.

That is, the first aspect of the present invention provides a process of separating pentafluoroethane out of a gas mixture which contains at least perchloroethylene, pentafluoroethane, hydrogen chloride and hydrogen fluoride, characterized in that the process comprises the steps of:

a) passing the gas mixture through the first condensation stage to obtain the first liquid phase which contains, as a main component, perchloroethylene contained in the gas mixture and the first vapor phase which contains the rest of the gas mixture, b) passing the first vapor phase through the second condensation stage to obtain the second vapor phase which contains pentafluoroethane and hydrogen chloride as main components and the second liquid phase which contains the rest of the first vapor phase, c) introducing the second liquid phase to a distillation stage to separate it into a top fraction which contains pentafluoroethane and hydrogen chloride as main components and a bottom fraction which contains the rest of the second liquid phase and which is substantially free from pentafluoroethane and hydrogen chloride, and d) removing hydrogen chloride out of the second vapor phase and the top fraction to obtain pentafluoroethane, and the second liquid phase has a composition with which it does not separate into immiscible liquid phases.

Whether or not the second liquid phase separates into the immiscible liquid phases depends on its temperature and its composition. Thus, changes of these two factors may have effects on whether or not the second liquid phase separates into the immiscible liquid phases (this phenomenon is herein sometimes referred to as "liquid separation" or "phase separation"). Determination whether or not the second liquid phase causes the liquid separation may be carried out by actually preparing a liquid which corresponds to the second liquid phase, actually subjecting the liquid to conditions (particularly a temperature) to which the second liquid phase is expected to be subjected, and then confirming whether or not the liquid causes the liquid separation.

Within industrially employed operative conditions, the present inventors have found that a PCE concentration of the second liquid phase may be used as a more convenient measure with which occurrence of the liquid separation is determined. That is, under the industrially employed operative conditions, the liquid separation depends on concentration relationships among HF, HFC-125 and PCE. Roughly speaking, it has been found that when the PCE concentration of the second liquid phase is not more than about 3% by mole and preferably not more than about 1% by mole, the second liquid phase does not separate into the immiscible liquid phases, based on which thus the present invention has been made.

Figure 1:
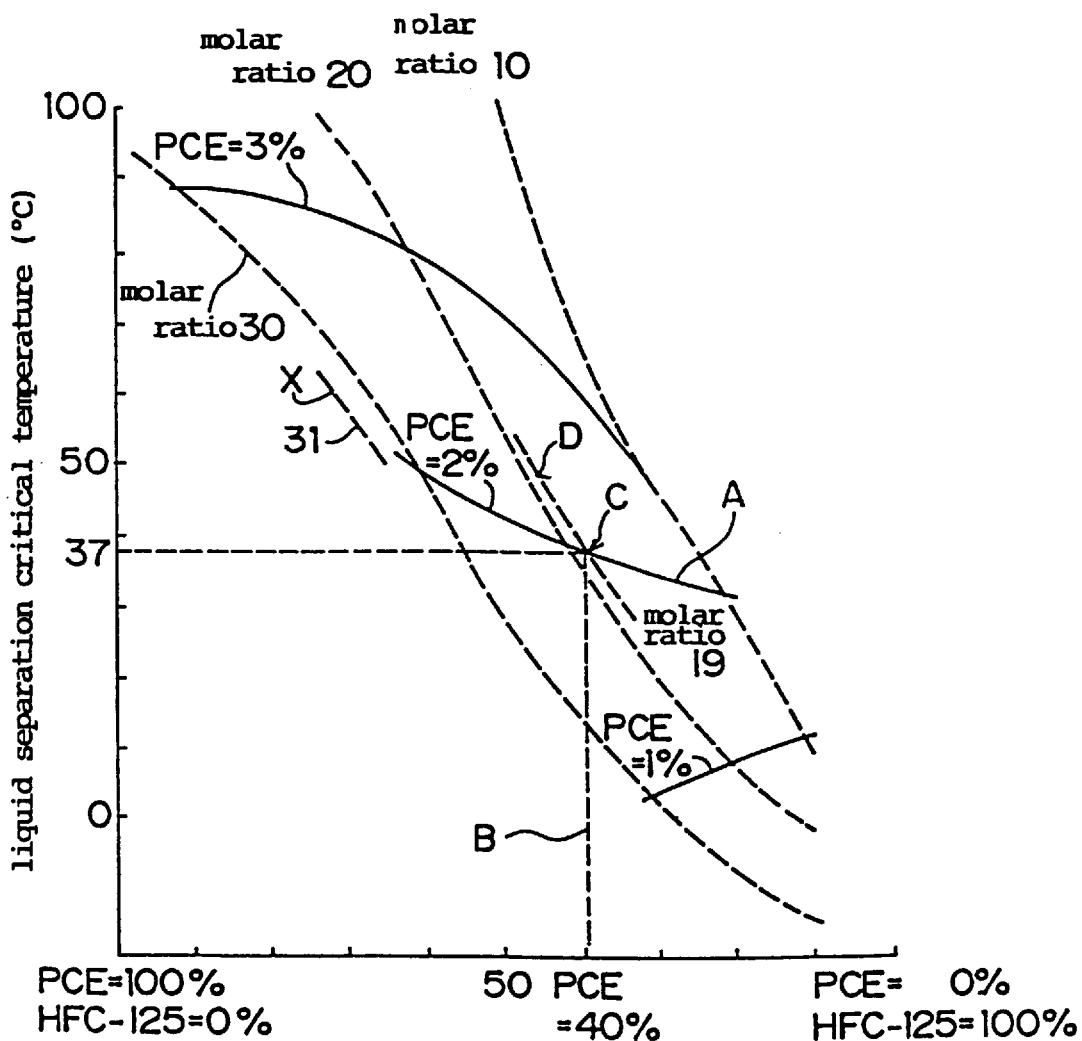
FIG. 1 shows a graph in which liquid—liquid equilibrium curves of a ternary component system of PCE, HFC-125 and HF which indicate critical temperatures at which the system starts to separate into immiscible liquid phases.

In the drawings, the numerals indicate the following:

| | |
|---|---|
| 1. reactor | 2. gas mixture stream |
| 3. first condenser | 4. first liquid phase |
| 5. first vapor phase stream | 6. compressor |
| 7. second condenser | 8. second liquid phase |
| 9. second vapor phase stream | 10. distillation apparatus |
| 11. bottom fraction | 12. top fraction |
| 13. distillation apparatus | 14. bottom fraction stream |
| 15. top fraction stream | |

DETAILED DESCRIPTION OF INVENTION

Operation conditions under which the second liquid phase has such a composition that it does not separate into the immiscible liquid phases are easily selected by confirming occurrence or non-occurrence of the liquid separation when the second liquid phase is subjected to expected operation conditions (concretely, a pressure and a temperature under which the second liquid phase can exist as liquid, and usually only the temperature since liquid separation is not substantially affected by the pressure), as described above. Reversely, when the operation conditions have been already fixed, a temperature at which the liquid separation does not occur may be selected by changing a composition of the second liquid phase differently.

However, as a more convenient measure, considering limitation as to industrially available operation conditions (such as a temperature and a pressure) based on liquid-liquid equilibriums of a ternary component system of PCE, HFC-125 and HF, a critical composition for the liquid separation may be optimally selected on the basis of the operation conditions preliminary fixed, or a critical temperature for the liquid separation may be optimally selected on the basis of the second liquid phase composition preliminary fixed. In this case, a key component which may be conveniently used is actually PCE as described above. When a PCE concentration is above a certain concentration In the ternary component system under predetermined operation conditions, a liquid of the system separates into the immiscible liquid phases.

In the process according to the present invention, the gas mixture contains HCl. When an amount of HCl contained in the second liquid phase is small, for example when an HCl concentration in the second liquid phase is not more than about 0.8% by mole and preferably not more than about 0.5% by mole, it is sufficient only to consider the liquid-liquid equilibriums of the ternary component system as described above and no substantial problem occurs in industrial operations.

The liquid-liquid equilibriums of the ternary component liquid system may be obtained by theoretical calculations or making experiments. For example, FIG. 1 shows a graph of the liquid—liquid equilibriums of the three components based on the theoretical calculations which shows a temperature at which liquid starts to separate into the immiscible liquid phases. In the graph, the abscissa axis indicates a percent ratio by mole of PCE or HFC-125 to PCE and HFC-125 (namely only organic components are included in the consideration), namely the right end of the abscissa axis corresponds to 100% by mole of HFC-125, and the left end of the abscissa axis corresponds to 100% by mole of PCE. The ordinate axis indicate a critical temperature at which the system begins to separate into the two immiscible liquid phases (a phase separation temperature). The numerals near the solid lines show percentages by mole of PCE based on the ternary component system total (i.e. [PCE/(PCE+HFC-125+HF)]×100). Further, the numerals near the broken lines show molar ratios (i.e. ratios based on mole) of HF to (PCE+HFC-125) (i.e. HF/(PCE+HFC-125)).

In the graph, the solid lines and the broken lines correspond to sets of critical temperatures at which the phase separation starts to begin (namely, a temperature at which a liquid system having a given composition starts to separate into the immiscible liquid phases), and no immiscible liquid phases are present at a temperature in regions above the solid lines or the broken lines. For example, let us assume a ternary component system of PCE, HFC-125 and HF having a molar ratio (a ratio by mole) of 2:3:95. The ternary component system has a molar ratio of PCE to HFC-125 of 2:3 (=40:60) and a PCE concentration of 2% by mole based on the ternary component system total. A composition of the ternary component system is indicated by an intersecting point C between a critical phase separation line for 2% of PCE (solid line A) and a vertical straight line passing a point of 40% of PCE (dotted line B). Thus, in this case, when the system is at a temperature above about 37° C., the system does not exhibit the liquid separation. Reversely, when the system is at a temperature below about 37° C., the system separates into the immiscible liquid phases. Alternatively, since the PCE concentration is 2% by mole and a molar ratio of HF to (PCE and HFC-125) is 19 (=95/(2+3)), the critical point may be obtained as an intersecting point C between the solid line A and the broken line D (for the molar ratio of 19). In addition, the critical point may be obtained as an intersecting point between the dotted line B and the broken line D.

The liquid—liquid equilibriums shown in FIG. 1 were obtained by the theoretical calculations using basic physical properties and observed values of each compound as well as a software "Aspen Plus" created by Aspen Tech Japan Co. (Atlas Building, Ichibancho 5, Chiyoda-ku, Tokyo, Japan).

Various compositions of the second liquid phase are estimated by carrying out the first condensation stage under various conditions so as to obtain a composition and an amount of the first vapor phases (by calculating theoretically or making experiments) and then carrying out the condensation of the first vapor phases (i.e. the second condensation stage) based on operation conditions and vapor-liquid equilibriums while making try-and-error experiments or the theoretical calculations. Comparison of a critical temperature for thus estimated composition which is obtained from the graph of FIG. 1 with a predetermined temperature of the second liquid phase can make it possible to determine whether or not the second liquid phase separates into the immiscible liquid phases. Such estimation of the composition of the second liquid phase as described above is readily carried out by those skilled in the art, especially in the field of the chemical engineering.

For example, a composition and an amount of the first vapor phase obtained from the first condensation stage are firstly determined, and then a composition of the second liquid phase which is obtained by condensing the first vapor phase is estimated based on various operation conditions and liquid-vapor equilibriums. Then, it is easily determined whether or not thus estimated second liquid phase separates into the immiscible liquid phases considering the graph of FIG. 1 similarly to the example just described above. Reversely, since a relationship between a composition and a temperature has been known with which the second liquid phase does not separate into the immiscible liquid phases, it is also possible to determine how much amount of the first vapor phase is to be condensed in the second condensation step or at which temperature the first vapor phase is to be condensed. In order to carry out the above determinations, vapor-liquid equilibriums and liquid—liquid equilibriums of the ternary component system are necessary, and those skilled in the art can easily carry out the determinations.

In one particularly preferred embodiment of the first aspect according to the present invention, the process of separating HF out of the gas mixture which contains at least PCE, HFC-125, HCl and HF is characterized in that the process comprises the steps of:

a) passing the gas mixture through the first condensation stage to obtain:

the first liquid phase which contains as a main component PCE contained in the gas mixture and preferably of which PCE concentration is at least 60% by mole, and the first vapor phase which contains the rest of the gas mixture;

b) passing the first vapor phase through the second condensation stage to obtain:

the second vapor phase which contains HFC-125 and HCl as main components and preferably of which HCl plus HFC-125 concentration is at least 80% by mole, and the second liquid phase which contains the rest of the first vapor phase;

c) introducing the second liquid phase to the distillation stage to separate into:

the top fraction which contains HFC-125 and HCl as main components and preferably of which HCl plus HFC-125 of concentration is at least 90% by mole, and the bottom fraction which is substantially free from HCl and HFC-125 and preferably of which HCl plus HFC-125 concentration is not more than 3% by mole, and the bottom fraction which contains the rest of the second liquid phase; and d) removing HCl out of the second vapor phase and the top fraction so as to obtain HFC-125, and when a molar ratio (a ratio by mole) of PCE:HFC-125 of the second liquid phase is in the range between about 100:0 and 50:50, a PCE concentration of the second liquid phase is not larger than a certain concentration within the range between about 2.5 and 3% by mole and a condensation temperature of the second condensation stage is not lower than a certain temperature within the range between about 70° and 90° C., when a molar ratio (a ratio by mole) of PCE:HFC-125 of the second liquid phase is in the range between about 50:50 and 20:80, a PCE concentration of the second liquid phase is not larger than a certain concentration within the range between about 2 and 3% by mole and a condensation temperature of the second condensation stage is not lower than a certain temperature within the range between about 30° and 70° C., or when a molar ratio (a ratio by mole) of PCE:HFC-125 of the second liquid phase is in the range between about 20:80 and 0:100, a PCE concentration of the second liquid phase is not larger than a certain concentration within the range between about 1 and 3% by mole and a condensation temperature of the second condensation stage is not lower than a certain temperature within the range between about −20° and 30° C., and the second liquid phase does not separate into the immiscible liquid phases under the above temperature and concentration conditions.

In the present specification, when "a certain concentration within the range . . . " and "a certain temperature within the range . . . " are used, they are intended to mean a combination of a concentration as a critical concentration and a temperature as a critical temperature (i.e. a critical liquid separation composition or a critical liquid separation temperature) within the defined ranges, with which combination the second liquid phase starts to separate into the immiscible liquid phases. Such a combination can be obtained from the liquid—liquid equilibriums as shown in FIG. 1.

More concretely, the compositions of the second liquid phase and the critical liquid separation temperatures (Crit. Sep. Temp.) for those compositions are exemplified as follows:

| No. | % PCE[1] | Molar Ratio[2] | Crit. Sep. Temp (°C.) |
|---|---|---|---|
| 1 | 5 | 10 | 4 |
| 2 | 5 | 20 | −7 |
| 3 | 10 | 10 | 7 |
| 4 | 10 | 20 | −3 |
| 5 | 15 | 10 | 19 |
| 6 | 15 | 20 | 2 |
| 7 | 20 | 10 | 26 |
| 8 | 30 | 12 | 38 |
| 9 | 40 | 12 | 59 |
| 10 | 50 | 15 | 73 |
| 11 | 60 | 20 | 76 |
| 12 | 70 | 20 | 93 |
| 13 | 80 | 20 | 100 |
| 14 | 90 | 30 | 86 |

[1] % PCE = [PCE/(PCE + HFC-125)] × 100 (based on mole)
[2] Molar Ratio = HF/(PCE + HFC-125) (based on mole)

As described above, once the liquid composition has been selected, the critical liquid separation temperature for the composition is obtained. Thus, when the second liquid condensation is operated at a temperature above such a critical temperature, the second liquid phase does not separate into the immiscible liquid phases.

When an HCl concentration is small in the second liquid phase, operation conditions of the present process may be selected based on the equilibrium relationships for the ternary component system as described above. However, when the HCl concentration is increased, for example when the HCl concentration exceeds 0.5% by mole and particularly when the HCl concentration exceeds 0.8% by mole in the second liquid phase, HCl may have some effect on the operation conditions of the second condensation stage.

In the present process, a considerable amount of PCE is removed through the first condensation stage, so that a PCE concentration is not so large in the first vapor phase. It is thus expected that a PCE concentration in the second liquid phase is also not so large. Therefore, when the effect of the presence of HCl on the operation conditions of the second condensation stage is taken into account, it is sufficient from an industrial view point to consider a right side of the graph in FIG. 1, preferably roughly a right half part of the graph in FIG. 1, and more preferably a region of which PCE % is between about 0 and 30% of the graph in FIG. 1.

According to the studies by the present inventors, when the PCE concentration is relatively small and particularly when the PCE % is not more than 30%, the effects of the presence of HCl on the second condensation stage are as follows:

(1) When the HCl concentration is not more than about 5% by mole in the second liquid phase, a critical liquid separation temperature is reduced by about 5° to 30° C. from the critical liquid separation temperature which is obtained based on the ternary component system assuming that HCl is absent;

(2) When the HCl concentration is in the range between about 5 and 10% by mole in the second liquid phase, a critical liquid separation temperature is reduced by about 20° to 80° C. from the critical liquid separation temperature which is obtained based on the ternary component system assuming that HCl is absent; and (3) When the HCl concentration is not less than about 10% by mole in the second liquid phase, a critical liquid separation temperature is reduced by at least about 30° C. from the critical liquid separation temperature which is obtained based on the ternary component system assuming that HCl is absent.

As seen from the above, the presence of HCl reduces the liquid separation temperature at least in the region of the right half part and particularly in the range of 0<PCE %<about 30 of the graph of FIG. 1. That is, the critical liquid separation temperature of the ternary component system in which HCl is absent is higher by at least about 5° C. than that of the four component system which additionally contains HCl. Therefore, when a condensation temperature of the second condensation stage is preliminarily selected for the ternary component system without HCl as shown in FIG. 1, the operation with thus preliminarily selected temperature avoids the liquid separation of the second liquid phase into the immiscible liquid phases even though HCl is additionally present. That is, the presence of HCl shifts the operation toward a safe side (i.e. fail-safe) in the process of the present invention, and thus it does not have adversely effect on the second condensation stage at all.

In one concrete example of the process according to the present invention, in order to prevent the PCE concentration of the second liquid phase from being above 3% by mole, condensation conditions of the steps a) and b) are appropriately selected depending on the composition of the gas mixture. For example, most of and preferably at least about 60% of the gas mixture is removed as the first liquid phase, which reduces a ratio of PCE contained in the first vapor phase is reduced. Then, even if such PCE is present in the second liquid phase, the PCE concentration in the second liquid phase does not exceed the critical concentration which is obtained based on the liquid—liquid equilibriums (i.e. a concentration corresponding to a border temperature between the occurrence and the non-occurrence of the liquid separation into the immiscible liquid phases). For example, the PCE concentration does not become larger than 3% by mole and preferably 2% by mole based on the ternary component system of HF, HFC-125 and PCE. With such a concentration, a mixture consisting essentially of PCE, HF, HCl and HFC-125, namely the second liquid phase does not separate into the immiscible liquid phases at a temperature in the range between about −20° C. and 90° C.

Thus, the distillation in the step c) may be carried out using a single distillation apparatus, which solves the problem as described in the background art description, namely the need to treat the upper layer and the lower layer separately.

The step d) of the present process may be carried out in any suitable known manner. For example, a water washing treatment may be used to separate into hydrogen chloride and HFC-125.

In the present process, the gas mixture which contains at least PCE, HFC-125, hydrogen chloride and HF is preferably a gas produced from a reaction step in which PCE and HF are reacted to produce HFC-125.

In the present process, the gas mixture may further comprise HFC-123 and HFC-124. In this case, HFC-123 and HFC-124 do not substantially affect the separation process described above. That is, even when those components are present, the second liquid phase does not separate into the immiscible liquid phases so that effects of the present invention are obtained unless the PCE concentration in the second liquid phase exceeds the critical concentration (based on the ternary component system of HF, HFC-125 and PCE), for example about 3%. The coexistent HFC-123 and HFC-124 are merely distributed to a distillate fraction and a bottom fraction in each step depending on operation conditions and vapor-liquid equilibriums with the other components.

Thus, the second aspect of the present invention provides a process of producing HFC-125 by reacting PCE and HF characterized in that the process comprises the steps of:

(1) reacting PCE and HF under HFC-125 producing conditions to obtain a gas mixture which comprises at least PCE, HFC-125, HCl, HFC-123, HFC-124 and HF, (2) passing the gas mixture through the first condensation stage to obtain the first liquid phase which contains, as a main component, PCE contained in the gas mixture and the first vapor phase which contains the rest of the gas mixture, (3) passing the first gas phase through the second condensation stage to obtain the second vapor phase which contains HFC-125 and HCl as main components and the second liquid phase which contains the rest of the first vapor phase, (4) introducing the second liquid phase to a distillation stage to separate into a top fraction which contains mainly HFC-125 and HCl as main components and a bottom fraction which is substantially free from HFC-125 and HCl and which contains the rest of the second liquid phase, and (5) removing HCl from the second vapor phase and the top fraction to obtain HFC-125, and the second liquid phase has such a composition that it does not separate into immiscible liquid phases.

That is, the HFC-125 separation process of the first aspect described above is used in the production process of HFC-125 of the present invention.

The step (1) of the production process of the present invention in which PCE and HF are reacted under the HFC-125 producing conditions to obtain a gas mixture which comprises at least PCE, HFC-125, HCl, HFC-123, HFC-124 and HF is well-known, and U.S. Pat. No. 4,766,260 may be referred to for the production. Usual conditions for the reaction may include a molar ratio of $HF/CCl_2=CCl_2$ in the range between 7 and 20, a reaction temperature of 340° C. and a contact time of the reactants in the range between 20 and 90 seconds.

The first condensation stage is a stage in which so-called partial condensation is carried out, and a conventional condensers may be used for this stage. Operation conditions for the condenser may be properly selected by those skilled in the art depending on the composition of the gas mixture.

It is generally preferable to condense PCE as much as possible through the first condensation stage because the PCE concentration of the second liquid phase formed in the second condensation stage is likely to be high when an amount of PCE in the first vapor phase is large. Thus, in a more preferably embodiment, substantially only PCE (preferably at least 60% by mole of PCE) is obtained as the first liquid phase in the first condensation stage.

As usual operation conditions for the first condensation stage, an operation pressure of 40 kgf/cm$^2$-abs. or less, and preferably 20 kgf/cm$^2$-abs. and a condensation temperature between −50° C. and 100° C., and preferably between −30° C. and 50° C. may be used. When the first condensation stage is carried out under such operation conditions, the first liquid phase includes at least about 70% and preferably at least about 90% of PCE contained in the gas mixture produced from the reaction of PCE with HF. The first liquid phase is preferably recycled to the reaction stage.

The second condensation stage is also a stage in which the partial condensation is carried out as in the first condensation stage. In the second condensation stage, it should be noted that the PCE concentration of the second liquid phase formed by the condensation is required to be not above the critical concentration, not above about 3% by mole, preferably not above about 2% by mole, and more preferably not above about 1% by mole based on the total moles of PCE, HFC-125 and HF. This is because the second liquid phase does not separate into the immiscible liquid phases under industrially feasible operation conditions (including a composition) at a condensation temperature within the range between about 30° and 90° C. when not above such a critical composition. That the second liquid phase does not separates into the immiscible liquid phases make it advantageously possible to subject the second liquid phase to a single distillation stage. At the same time, the second vapor phase preferably is required to consists substantially of hydrogen chloride and HFC-125. In order to satisfy both of the requirement of the second vapor phase and also the PCE requirement of the second liquid phase, it is convenient to remove PCE as much as possible through the first condensation stage since the requirements in the second condensation stage are easily satisfied through such removal.

As usual operation conditions for the second condensation stage, an operation pressure of 40 kgf/cm$^2$-abs. or less and preferably in the range between 3 kgf/cm$^2$-abs. and 20 kgf/cm$^2$-abs. and a condensation temperature between −50° C. and 80° C., and preferably between −30° C. and 40° C. may be used. When the second condensation stage is carried out under such operation conditions, it is possible that the second vapor phase consists substantially of hydrogen chloride and HFC-125 (preferably an amount of the both components together is at least about 80% by mole) and the PCE concentration in the second liquid phase is below the critical concentration, for example not more than 3% by mole.

The distillation stage of the present invention divides the second liquid phase into the top fraction which consists substantially of hydrogen chloride and HFC-125 (preferably a concentration of these components together is at least 90% by mole) and the bottom fraction which does not substantially contain hydrogen chloride and HFC-125 (preferably a concentration of these components together is at most 3% by mole). This distillation stage is preferably carried out using a conventional pressurized distillation apparatus. Operation conditions and apparatus to form the fractions as described above may be easily selected by those skilled in the art based on the composition of the second liquid phase and specifications of the fractions. Usual operation conditions for this distillation stage includes an operation pressure in the range between 20 kgf/cm$^2$-abs. and 40 kgf/cm$^2$-abs. and a reflux ratio between about 2 and 5. The bottom fraction which does not substantially contain HFC-125 and HCl is desirably recycled to the reaction step.

Generally, the condensation stages and the distillation stage of the present invention are preferably carried out under pressurized conditions, otherwise a cooling medium is required which is of a considerably low temperature in those stages. In a pressurized operation, a compressor or a pump is used for pressurizing from a view point of facility simplicity or efficiency. In the process of the present invention, since a large amount of a high boiling component (perchloroethylene) is removed in the first condensation stage, it is advantageously easy to pressurize the first vapor phase using a compressor.

When the gas mixture is a reaction mixture from the reaction of PCE and HF, it also contains HFC-123, HFC-124 and HCl as by-products. Amounts of these components in the gas mixture depend on operation conditions of the reaction. Usually, an HCl concentration is about 16–50% by mole, an HFC-123 concentration is about 1–20% by mole, an HFC-124 concentration is about 2–20% by mole and an HFC-125 concentration is about 2–20% by mole in the gas mixture. In most cases, a PCE concentration in the gas mixture is about 3–20% by mole and an HF concentration is about 30–76% by mole.

Further, When the gas mixture is the reaction mixture from the reaction of PCE and HF, it additionally contains fluoro-hydrocarbons and chlorofluoro-hydrocarbons such as 1,1,1,2-tetrafluoroethane and 1,1-dichlorotetrafluoroethane. Usually, since these components are present in small amounts, they do not substantially affect the process of the present invention.

In any case, the first condensation stage and the second condensation stages may have a distillation function. That is, since any condensation stage separates a predetermined component or a mixture of such components out of the gas mixture, such separation becomes more effective when the stage not only has a simply condensing function of the gas but also additionally has a rectification function.

In a particularly preferable embodiment of the present invention, the second condensation stage has also a function of a distillation stage. That is, the first vapor phase is introduced to a distillation apparatus as it is or after compression so as to obtain the top fraction and the bottom fractions. Since the condensation stage is one which separates a predetermined component or a mixture of such components out of the gas mixture, the separation becomes more effective when the stage not only has a function simply to condensate the gas so as to obtain the liquid phase and the remaining vapor phase but also additionally has a distillation or rectification function. In addition, the second condensation stage and the distillation stage may be integral together. In this case, the first vapor phase is supplied to the distillation stage to obtain the top fraction which does not substantially contain PCE (preferably a PCE concentration is at most 0.5% by mole) and the bottom fraction which does not substantially contain HFC-125 and hydrogen chloride (preferably a concentration of these two components total is at most 3% by mole). Since the top fraction contains HFC-125 as an aimed compound, it is subjected to a conventional separation-refinery treatment to obtain HFC-125. Since the bottom fraction contains HF as a main component (preferably at least 60% by mole) and does not substantially contain HFC-125 (preferably at most 3% by mole), the bottom fraction is preferably recycled to the reaction stage. In this embodiment, the bottom liquid fraction from the distillation stage corresponds to the second liquid phase.

Function

The processes of the present invention described above are based on the following observations:

When the liquid-liquid equilibriums were measured for the ternary component system of PCE, HF and HFC-125, the results were obtained as shown in the graph of FIG. 1.

Thus, it is seen that the mixture of the ternary component system does not substantially separate into the immiscible liquid phases within a rage between about −20° C. and 90° C. under the industrially operational conditions provided that the PCE concentration is not more than about 3% by mole. On the basis of these results, when the PCE concentration of the second liquid phase which contains these three components is above about 3% by mole, the second liquid phase separates into the two immiscible liquid phases. Then, each phases has to be treated separately.

Therefore, the separate treatments is eliminated by avoiding the separation into the immiscible liquid phases.

DESCRIPTION OF CONCRETE EMBODIMENT OF INVENTION

Figure 2:
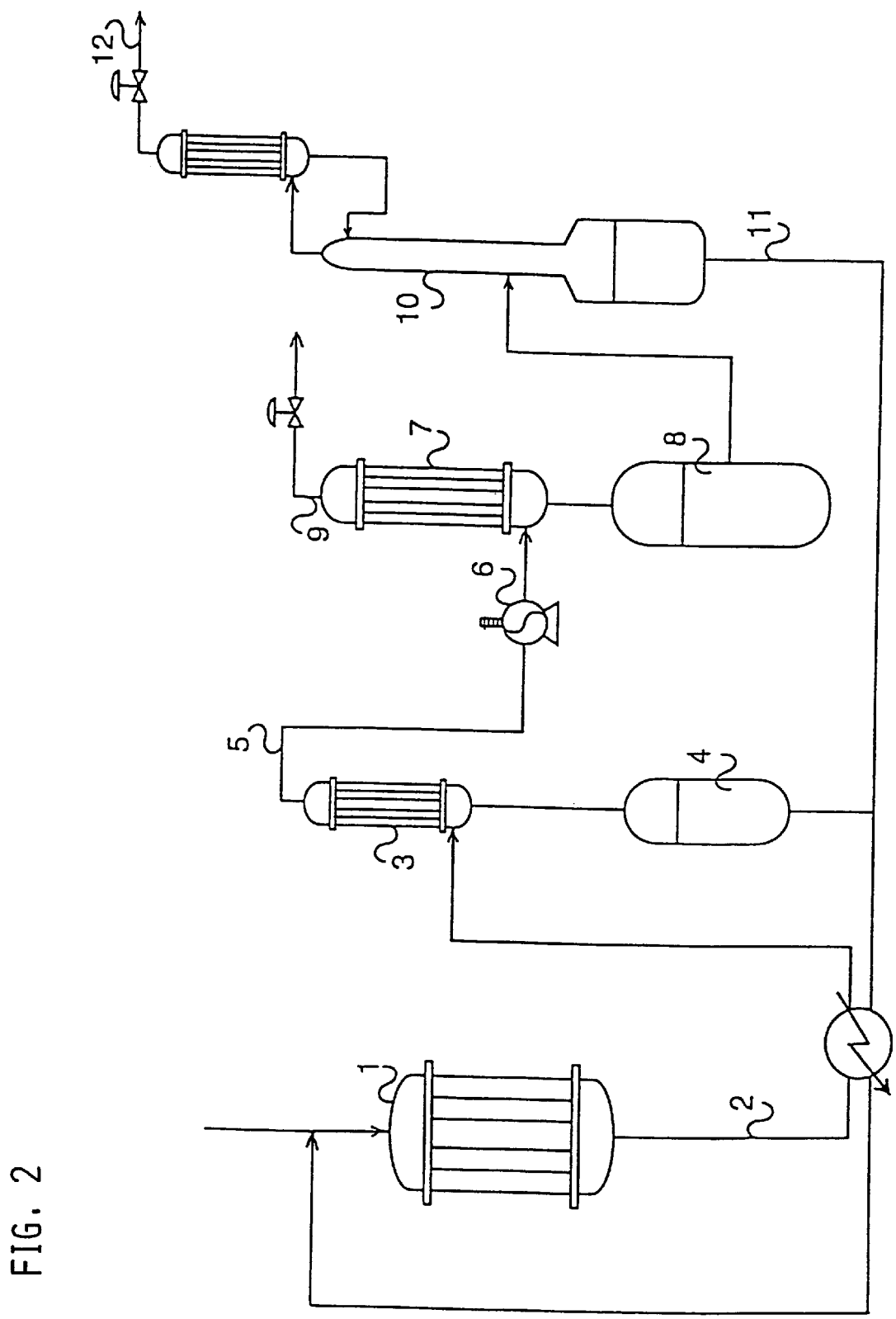
FIG. 2 shows a flow sheet of one embodiment of the process according to the present invention.

The process according to the present invention will be concretely explained below with reference to FIG. 2, which shows a flow sheet of a process of producing HFC-125 from HF and PCE.

HF and PCE react in a reactor 1 under predetermined conditions (for example, a temperature of 350° C. and a pressure of 1KG) to form a gas mixture stream 2 as a reaction product which contains HFC-125, HCl, HFC-123 and HFC-124 as well as unreacted HF and PCE. The gas mixture stream is passed to the first condensation stage comprising the first condenser 3 so as to condensate the stream (for example at a condensation temperature of 10° C. and a pressure of 1KG), whereby most of PCE, for example about 70% of PCE contained in the gas mixture is obtained as the first liquid phase 4 and a non-condensed gas is obtained as the first gas phase stream 5.

Then, the first vapor phase 5 is compressed (for example up to a pressure of 16 kgf/cm²-abs.) by a compressor 6 and then passed to the second condensation stage comprising the second condenser 7 for the condensation (for example at a condensation temperature of 10° C. and a pressure of 16 kgf/cm²-abs.) so that the rest of PCE contained in the first vapor phase is removed into the second liquid phase 8 and simultaneously a non-condensed gas is obtained as the second vapor phase stream 9 which does not substantially contain PCE.

The second liquid phase 8 contains a considerable amount of aimed HFC-125, which should be separated. For such separation, the second liquid phase 8 is passed to the distillation stage comprising a distillation apparatus 10.

The second liquid phase 8 is treated in the distillation apparatus 10 so as to separate it into the top fraction stream 12 which contain HFC-125 and hydrogen chloride as main components and the bottom fraction stream 11 which does not substantially contain HFC-125 and hydrogen chloride.

Since the bottom fraction 11 contains HF and the first liquid phase 4 contains PCE, they are recycled to the reactor 1 to re-use for the reaction.

Since the second vapor phase 9 and the top fraction stream 12 contains hydrogen chloride and small amounts of HFC-123 and HFC-124 in addition to aimed HFC-125, they are sent to a conventional separation process (such as a distillation process, not shown) together or separately for the separation.

Figure 3:
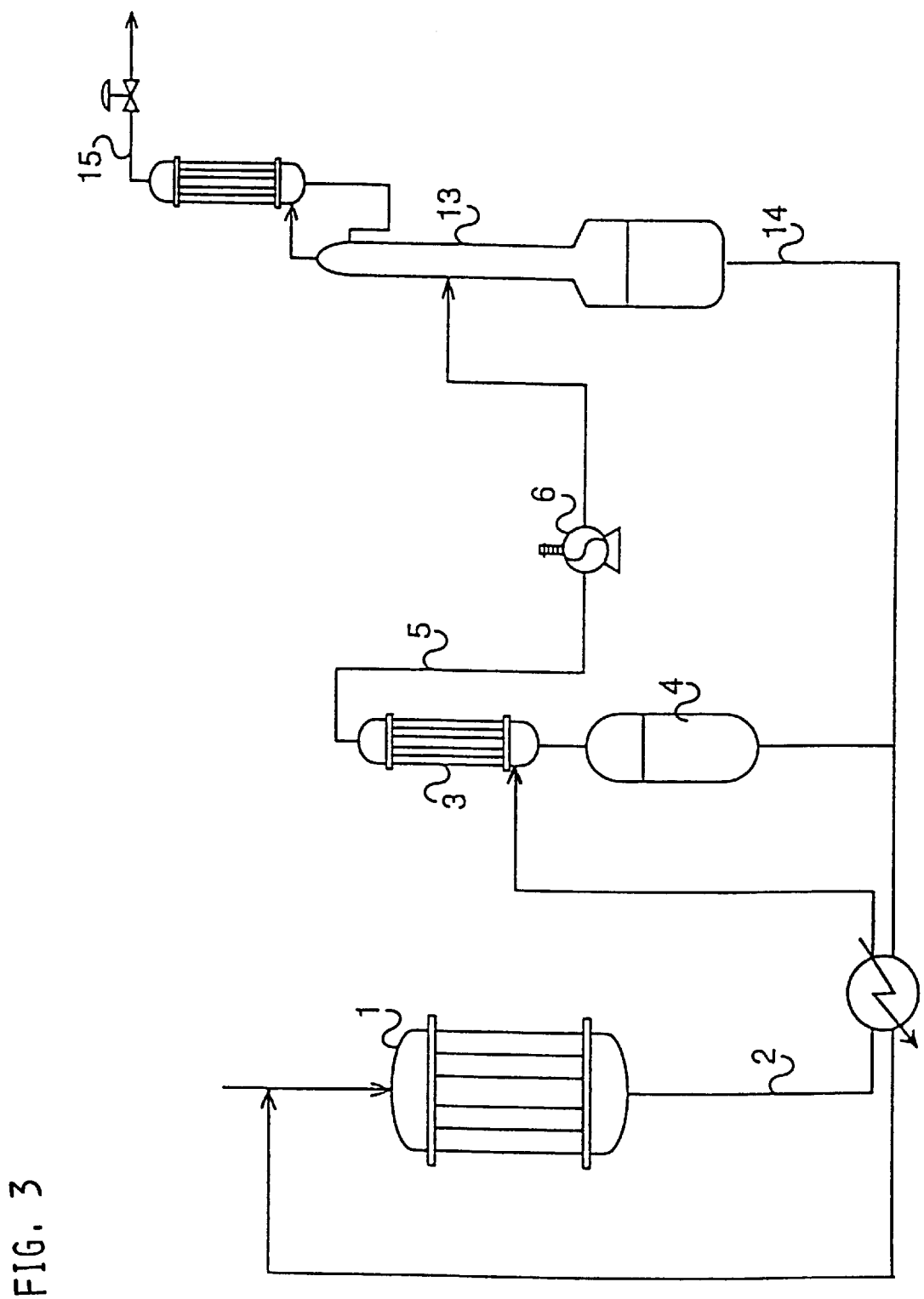
FIG. 3 shows a flow sheet of another embodiment of the process according to the present invention.

In another embodiment of the present invention, the first vapor phase 5 is directly supplied to the distillation apparatus 13 as shown in FIG. 3. That is, the second condensation stage and the distillation stage of FIG. 2 are integrally combined in FIG. 3. The distillation apparatus 13 separates the first vapor phase into the top fraction stream 15 which contains hydrogen chloride and HFC-125 as main components but which does not substantially contain PCE and the bottom fraction stream 14 which does not substantially contain HFC-125. The top fraction stream 15 is treated in a conventional step for the removal of hydrogen chloride, for example a distillation step so as to obtain HFC-125. The first liquid phase 4 and the bottom fraction stream 14 are recycled to the reactor 1 as in the embodiment shown in FIG. 2.

Effect of Invention

The process according to the present invention eliminates one distillation column from at least two distillation columns which have been expected to be necessary as described in the background art description.

EXAMPLES

Comparative Example 1

Figure 4:
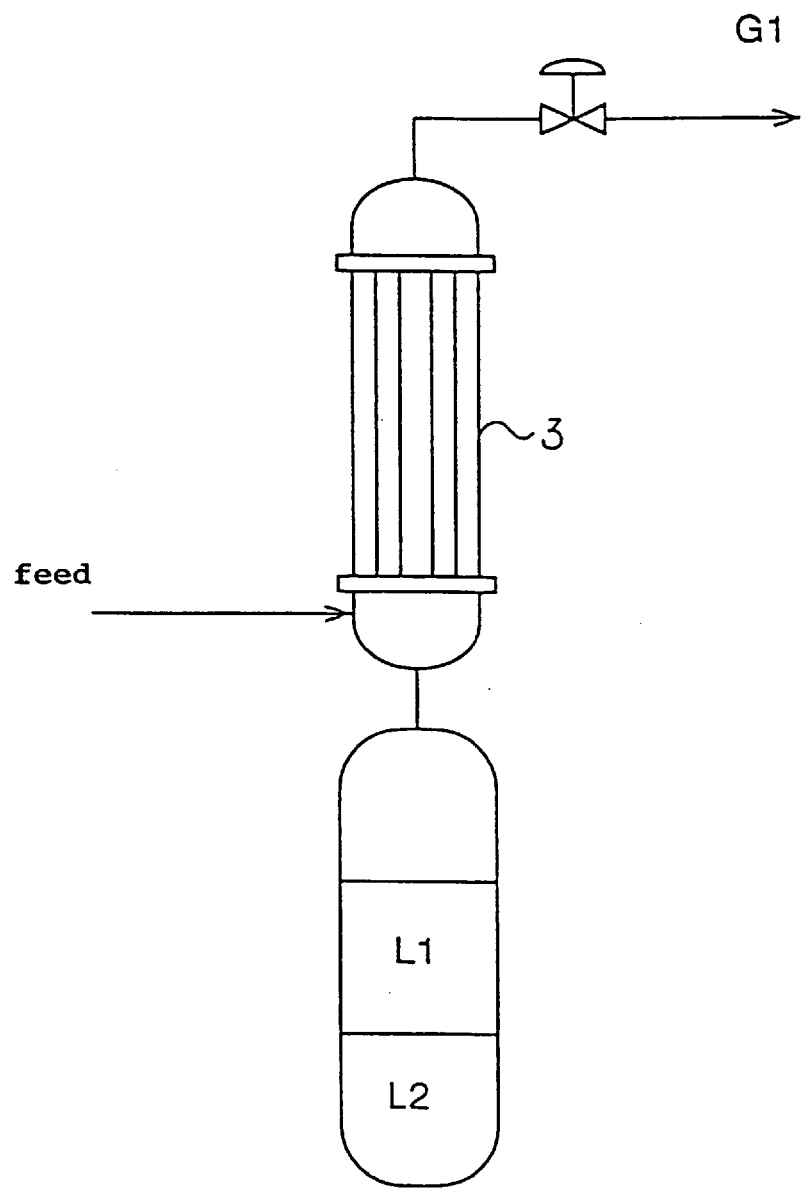
FIG. 4 schematically shows a flow sheet in which a process of Comparative Example 1 is schematically shown.

As schematically shown in FIG. 4, the gas mixture (Feed) having a composition shown in Table 1 was cooled to −25° C. at a pressure of 2.0 kgf/cm²-abs. in the condenser (3) to obtain the non-condensed fraction (G1) and the condensed fraction (liquid). The condensed fraction separated into the two immiscible layers (L1 and L2). Analyzing the non-condensed fraction and each layers, the results were obtained as shown in Table 1. Assuming that the two layers formed a single layer, a composition of such a single layer (L1+L2) was additionally calculated.

TABLE 1

| % by mole | Feed | G1 | L1 | L2 | L1 + L2 |
|---|---|---|---|---|---|
| HCl | 30.8 | 62.4 | 1.4 | 10.9 | 1.7 |
| HF | 59.3 | 23.6 | 94.5 | 13.3 | 92.0 |
| HFC-125 | 4.6 | 8.4 | 1.0 | 8.2 | 1.2 |
| HFC-124 | 3.0 | 4.1 | 1.6 | 15.8 | 2.0 |
| HFC-123 | 1.5 | 1.5 | 0.9 | 23.7 | 1.6 |
| PCE | 0.7 | trace | 0.5 | 28.0 | 1.4 |

Example 1

Figure 5:
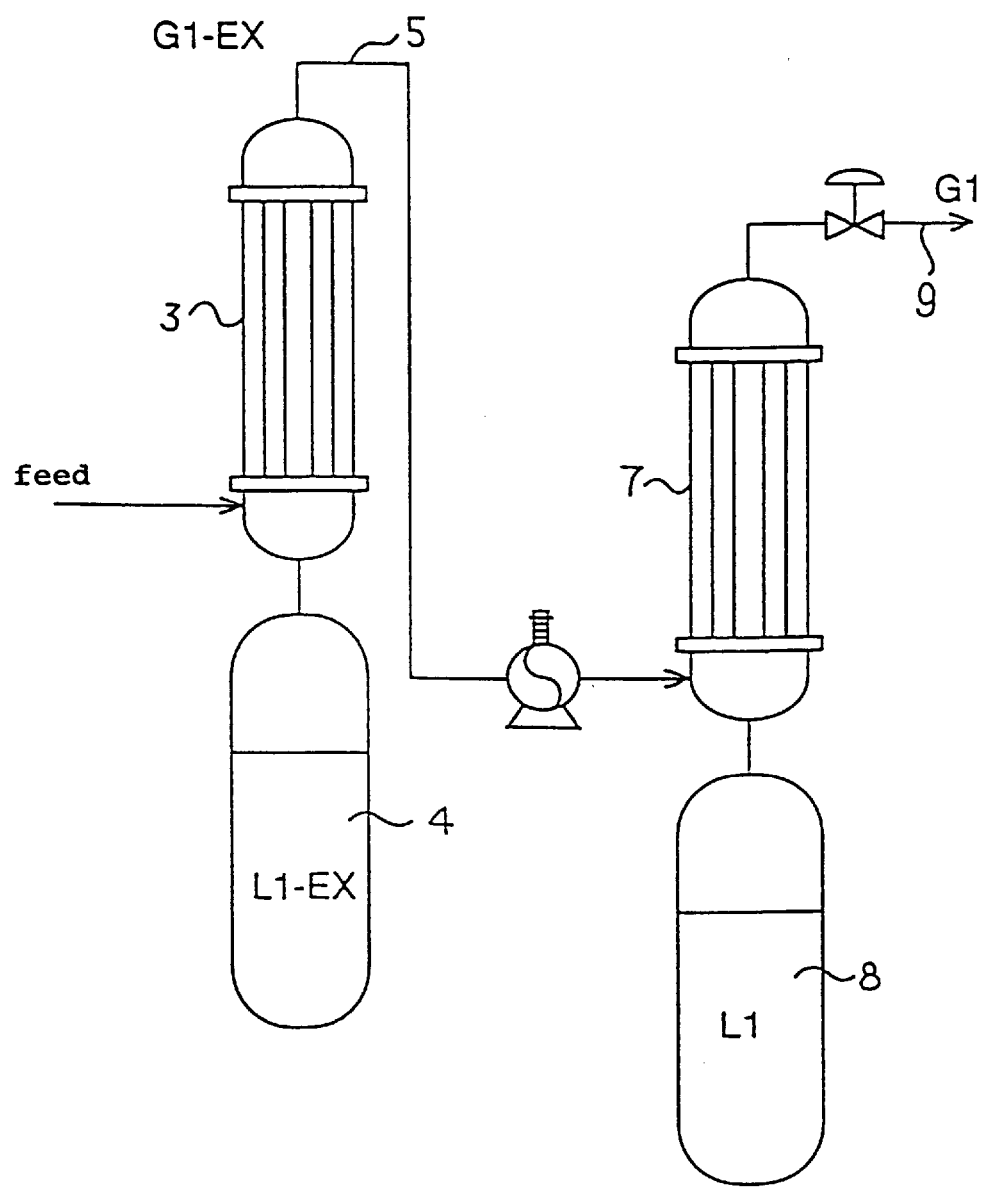
FIG. 5 schematically shows a flow sheet in which processes of Examples 1 and 2 are schematically shown.

As schematically shown in FIG. 5, the gas mixture having the same composition as in Comparative Example 1 was once cooled to 10° C. at a pressure of 2.0 kgf/cm²-abs. and a portion of PCE was condensed to obtain the first liquid phase (4) (L1-EX) and the first vapor phase (5) (G1-EX). Then, by passing the first vapor phase through a condensing apparatus (7), it was condensed at a temperature of 10° C. and at a pressure of 16.0 kgf/cm²-abs. using a compressor (6) to obtain the second liquid phase (8) and the second vapor phase (9). The non-condensed gas (the vapor phase) was withdrawn. The condensed liquid (the liquid phase) did not separate into immiscible liquid phases in the condensation apparatus 2. Compositions of the non-condensed gas (G1) and the condensed liquid (L1) are shown in Table 2 below.

TABLE 2

| % by mole | Feed | L1-EX | G1 | L1 |
|---|---|---|---|---|
| HCl | 30.8 | 3.1 | 82.7 | 10.1 |
| HF | 59.3 | 11.5 | 9.9 | 79.8 |
| HFC-125 | 4.6 | 1.8 | 4.8 | 4.6 |
| HFC-124 | 3.0 | 4.7 | 2.2 | 3.4 |
| HFC-123 | 1.5 | 9.8 | 0.5 | 1.9 |
| PCE | 0.7 | 69.0 | trace | 0.3 |

Example 2

The same procedures as in Example 1 were repeated except that the gas mixture had a different composition. The results are shown in Table 3 below.

TABLE 3

| % by mole | Feed | L1-EX | G1 | L1 |
|---|---|---|---|---|
| HCl | 33.0 | 1.5 | 82.7 | 12.3 |
| HF | 45.0 | 5.9 | 9.7 | 74.8 |
| HFC-125 | 5.2 | 0.9 | 5.3 | 6.2 |
| HFC-124 | 2.9 | 2.0 | 2.0 | 3.6 |
| HFC-123 | 1.8 | 4.1 | 0.4 | 1.9 |
| PCE | 12.1 | 85.5 | trace | 1.1 |

Example 3

Figure 6:
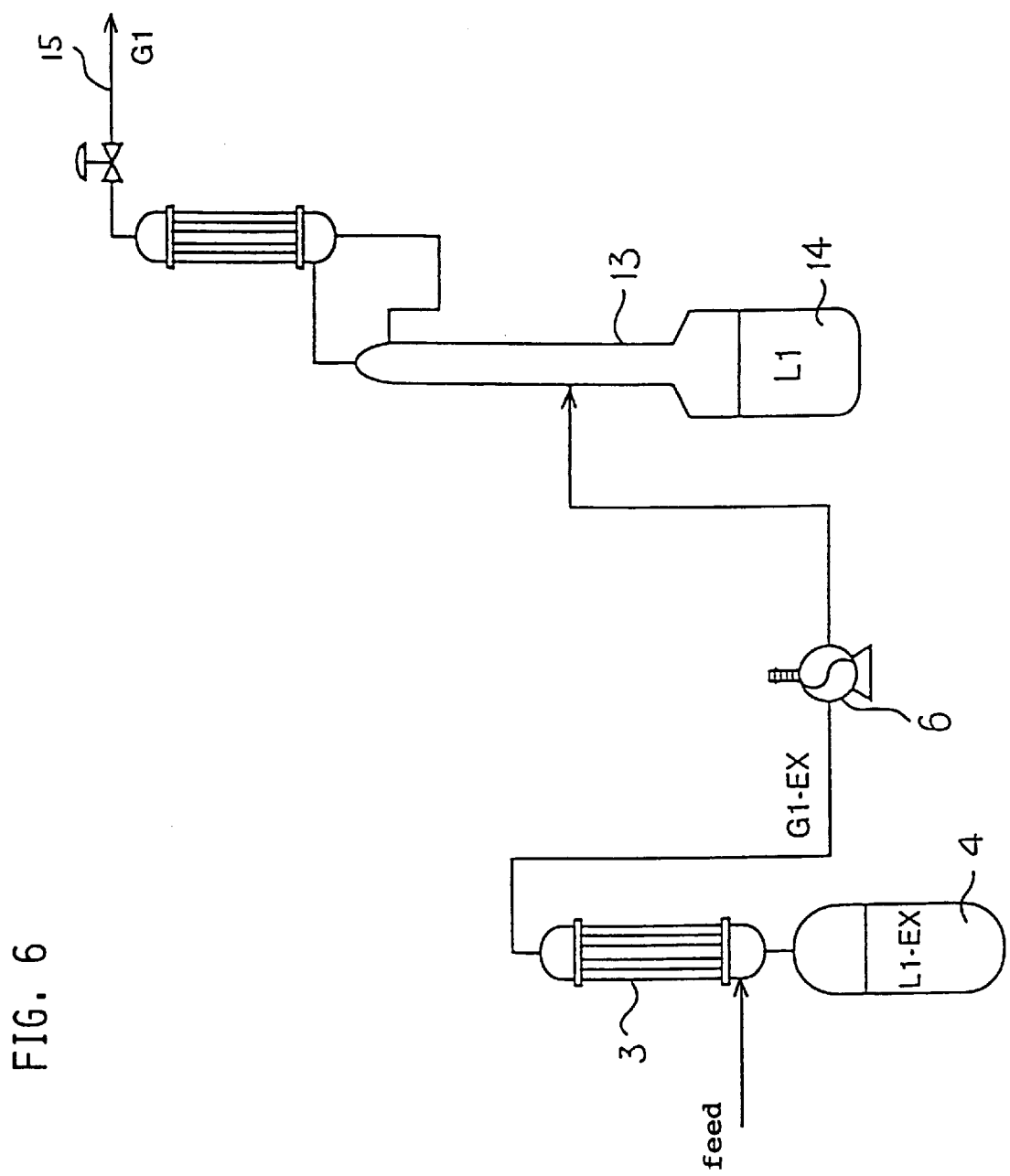
FIG. 6 schematically shows a flow sheet in which a process of Example 3 is schematically shown.

As schematically shown in FIG. 6, a gas mixture having the same composition as in Comparative Example 1 was once cooled to 10° C. at a pressure of 2.0 kgf/cm$^2$-abs. and a portion of PCE was condensed and liquified to obtain the first liquid phase (4) (L1-EX) and the first vapor phase (5) (G1-EX). Then, the first vapor phase was pressurized to 16.0 kgf/cm$^2$-abs. and introduced to a distillation column (13) so that the second vapor phase (15)(G1) was withdrawn from the top of the column. The second liquid phase (14)(L1, non-separated into immiscible liquid phases) was obtained from the bottom of the column. The results are shown in Table 4 below.

TABLE 4

| % by mole | Feed | L1-EX | G1 | L1 |
|---|---|---|---|---|
| HCl | 30.8 | 3.1 | 86.9 | 0 |
| HF | 59.3 | 11.5 | trace | 92.6 |
| HFC-125 | 4.6 | 1.8 | 13.0 | trace |
| HFC-124 | 3.0 | 4.7 | trace | 4.7 |
| HFC-123 | 1.5 | 9.8 | 0 | 2.3 |
| PCE | 0.7 | 69.0 | 0 | 0.4 |

As clearly seen from the results of Table 4, when the distillation apparatus is used for the second condensation step, the better results are obtained than when simple condensation is employed.

We claim:

1. A process of separating pentafluoroethane out of a gas mixture which contains components including at least perchloroethylene, pentafluoroethane, hydrogen chloride and hydrogen fluoride, said process comprising the steps of:
   a) passing the gas mixture through a first condensation stage to obtain a first liquid phase which contains, as a main component, perchloroethylene contained in the gas mixture and a first vapor phase which contains the other components of the gas mixture,
   b) passing the first vapor phase through a second condensation stage to obtain a second vapor phase which contains pentafluoroethane and hydrogen chloride as main components and a second liquid phase which contains the other components of the first vapor phase,
   c) introducing the second liquid phase to a distillation stage to separate the second liquid phase into a top fraction which contains pentafluoroethane and hydrogen chloride as main components and a bottom fraction which contains the other components of the second liquid phase and which is substantially free from pentafluoroethane and hydrogen chloride, and
   d) removing hydrogen chloride out of the second vapor phase and the top fraction of the second liquid phase to obtain pentafluoroethane,
   wherein the second liquid phase at the step b) does not separate into immiscible liquid phases.

2. The process according to claim 1 wherein a hydrogen chloride concentration of the second liquid phase is not larger than about 0.5%, and
   (1) when a ratio by mole of perchloroethylene:pentafluoroethane of the second liquid phase is in the range between about 100:0 and 50:50, a perchloroethylene concentration of the second liquid phase is not larger than a range between about 2.5 and 3% by mole and an operation temperature of the second condensation stage is not lower than a range between about 70° and 90° C., or
   (2) when a ratio by mole of perchloroethylene:pentafluoroethane of the second liquid phase is in the range between about 50:50 and 20:80, a perchloroethylene concentration of the second liquid phase is not larger than a range between about 2 and 3% by mole and an operation temperature of the second condensation stage is not lower than a range between about 30° and 70° C., or
   (3) when a ratio by mole of perchloroethylene:pentafluoroethane of the second liquid phase is in the range between about 20:80 and 0:100, a perchloroethylene concentration of the second liquid phase is not larger than a range between about 1 and 3% by mole and an operation temperature of the second condensation stage is not lower than a range between about −20° and 30° C.

3. The process according to claim 1 wherein a hydrogen chloride concentration of the second liquid phase is larger than about 0.5%, and an operation temperature of the second condensation stage is lower by at least about 5° C. than the condensation temperature of claim 2.

4. The process according to any one of claims 1 to 3 wherein the first vapor phase is pressurized by a compressor when it is passed to the second condensation stage.

5. A process of separating pentafluoroethane out of a gas mixture which contains components including at least perchloroethylene, pentaluoroethane, hydrogen chloride and hydrogen fluoride, said process comprising the steps of:
   a) passing the gas mixture through a first condensation stage to obtain a first liquid phase which contains, as a main component, perchloroethylene contained in the gas mixture and a first vapor phase which contains the other components of the gas mixture,
   b) introducing the first vapor phase to a distillation stage to separate the first vapor phase into a top fraction which contains pentafluoroethane and hydrogen chloride as main components and a bottom fraction which contains the other components of the first vapor phase and which is substantially free from pentafluoroethane and hydrogen chloride, and c) removing hydrogen chloride out of the top fraction to obtain pentafluoroethane.

6. A process of producing pentafluoroethane which comprises the steps of:
   (1) reacting perchloroethylene and hydrogen fluoride under pentafluoroethane producing conditions to obtain a gas mixture which comprises components including at least perchloroethylene, pentafluoroethane, hydrogen chloride, dichlorotrifluoroethane, tetrafluorochloroethane and hydrogen fluoride,
   (2) passing the gas mixture through a first condensation stage to obtain a first liquid phase which contains, as a main component, perchloroethylene contained in the gas mixture and a first vapor phase which contains the other components of the gas mixture,
   (3) passing the first vapor phase through a second condensation stage to obtain a second vapor phase which contains pentafluoroethane and hydrogen chloride as main components and a second liquid phase which contains the other components of the first vapor phase,
   (4) introducing the second liquid phase to a distillation stage to separate the second liquid phase into a top fraction which contains mainly pentafluoroethane and hydrogen chloride as main components and a bottom fraction which is substantially free from pentafluoroethane and hydrogen chloride and which contains the other components of the second liquid phase, and
   (5) removing hydrogen chloride from the second vapor phase and the top fraction of the second liquid phase to obtain pentafluoroethane,
   wherein the second liquid phase at the step (3) does not separate into immiscible liquid phases.

7. The process according to claim 6 wherein the first vapor phase pressurized by a compressor when it is passed to the second condensation stage.

8. The process according to claim 6 or 7 which further comprises the step of recycling the first liquid phase and the second liquid phase to the reaction step (1).

9. A process of producing pentafluoroethane which comprises the steps of:
   (1) reacting perchloroethylene and hydrogen fluoride under pentafluoroethane producing conditions to obtain a gas mixture which comprises components including at least perchloroethylene, pentafluoroethane, hydrogen chloride, dichlorotrifluoroethane, tetrafluorochloroethane and hydrogen fluoride,
   (2) passing the gas mixture through a first condensation stage to obtain a first liquid phase which contains, as a main component, perchloroethylene contained in the gas mixture and a first vapor phase which contains the other components of the gas mixture,
   (3) introducing the first vapor phase to a distillation stage to separate the first vapor phase into a ton fraction which contains mainly pentafluoroethane and hydrogen chloride as main components and a bottom fraction which is substantially free from pentafluoroethane and hydrogen chloride and which contains the other components of the first vapor phase, and
   (4) removing hydrogen chloride from the top fraction to obtain pentafluoroethane.

10. The process according to claim 9, which further comprises the step of recycling the first liquid phase to the reaction step (1).

* * * * *